United States Patent
Gustavsson

(10) Patent No.: US 7,065,406 B1
(45) Date of Patent: Jun. 20, 2006

(54) CARDIAC PACEMAKER UTILIZING PROLONGED A-V INTERVAL AND VENTRICULAR AUTOCAPTURE

(75) Inventor: Mikael Gustavsson, Lund (SE)

(73) Assignee: St. Jude Medical AB, Jarfalla (SE)

( * ) Notice: Subject to any disclaimer, the term of this patent is extended or adjusted under 35 U.S.C. 154(b) by 528 days.

(21) Appl. No.: 10/130,877

(22) PCT Filed: Sep. 19, 2000

(86) PCT No.: PCT/SE00/01817

§ 371 (c)(1),
(2), (4) Date: Sep. 23, 2002

(87) PCT Pub. No.: WO01/37927

PCT Pub. Date: May 31, 2001

(30) Foreign Application Priority Data

Nov. 22, 1999 (SE) .................................. 9904226

(51) Int. Cl.
*A61N 1/362* (2006.01)
(52) U.S. Cl. .......................................... 607/11; 607/28
(58) Field of Classification Search .................. 607/4, 607/9, 27–28

See application file for complete search history.

(56) References Cited

U.S. PATENT DOCUMENTS

| 5,282,838 A | 2/1994 | Hauser et al. |
| 5,601,615 A * | 2/1997 | Markowitz et al. ........... 607/28 |
| 6,618,622 B1 * | 9/2003 | Mann et al. .................. 607/28 |

FOREIGN PATENT DOCUMENTS

WO    WO 97/11746    4/1997

* cited by examiner

*Primary Examiner*—Robert E. Pezzuto
*Assistant Examiner*—Kritsen Mullen
(74) *Attorney, Agent, or Firm*—Schiff Hardin LLP

(57) ABSTRACT

A dual chamber cardiac pacemaker has a pulse controller for delivering stimulation pulses to the ventricle of a heart, a ventricular sensor for sensing ventricular depolarization, and a unit for identifying a beginning of an A-V interval of the heart. The pulse controller causes a ventricular stimulation pulse to be generated at a predetermined energy level after the expiration of a predetermined A-V interval. The controller prolongs the A-V interval under certain circumstances. Upon the expiration of the prolonged A-V interval, the pulse controller causes the ventricular pulse generator to emit a ventricular stimulation pulse at a higher energy level than the predetermined energy level to evoke a response in the ventricle. This allows the intrinsic heart activity to be detected and utilized, while ensuring safe pacing, as well as successful and reliable stimulation and maintaining a low power consumption during normal operation.

16 Claims, 3 Drawing Sheets

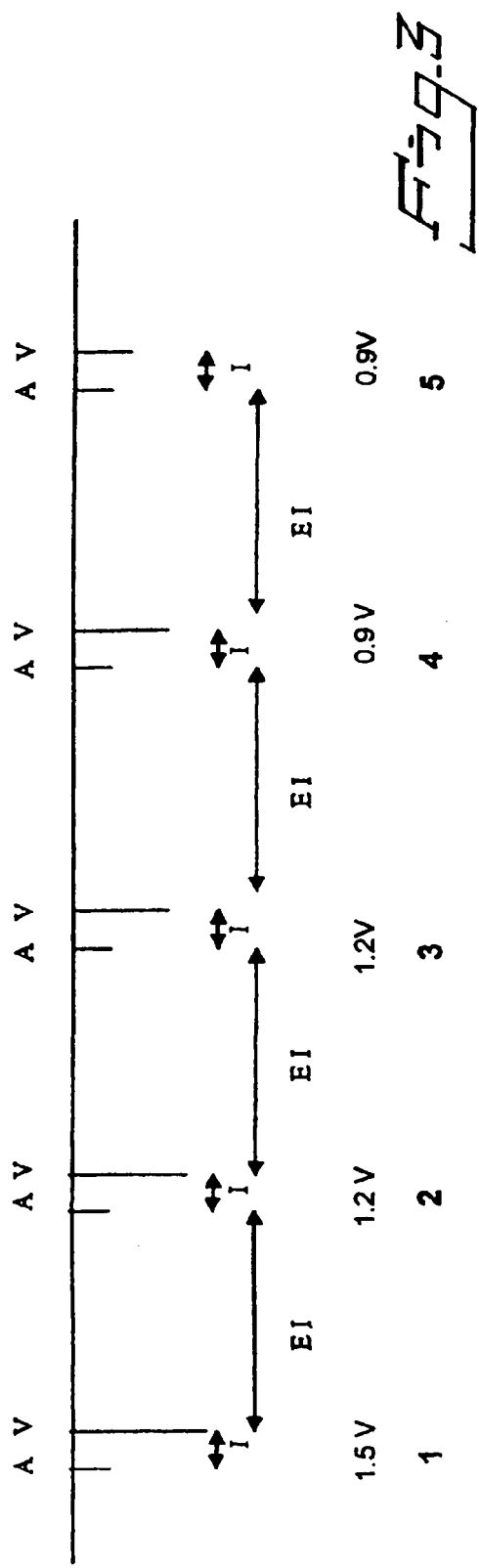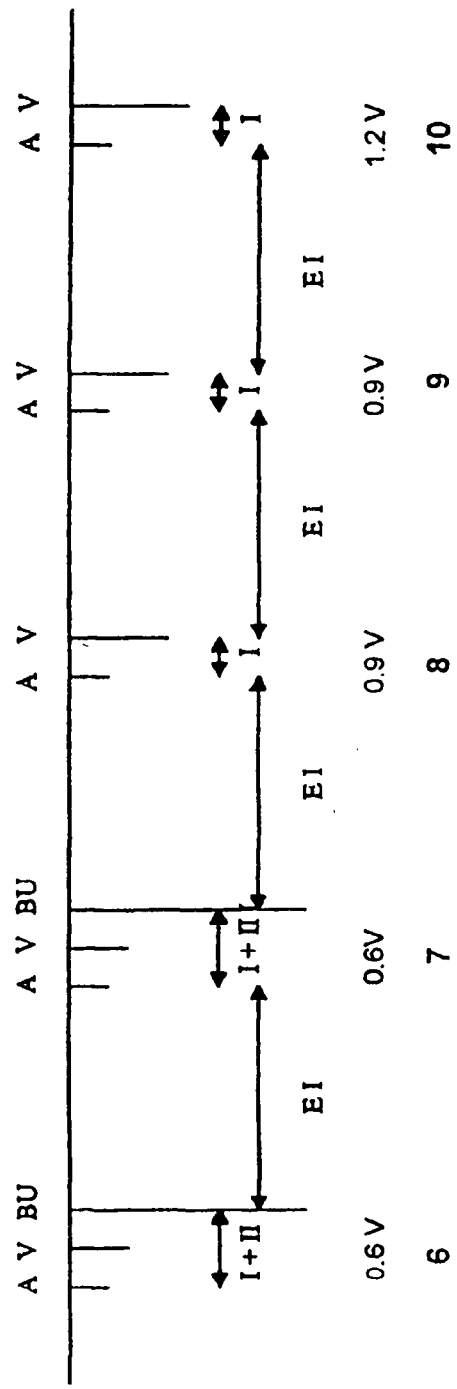
Fig. 3

CARDIAC PACEMAKER UTILIZING PROLONGED A-V INTERVAL AND VENTRICULAR AUTOCAPTURE

BACKGROUND OF THE INVENTION

1. Field of the Invention

The invention relates to cardiac pacers. It has specific relevance to pacers capable of operating in dual chamber mode with ventricular stimulation and sensing and at least one of atrial stimulation and atrial sensing.

2. Description of the Prior Art

Stimulation pulses emitted by cardiac pacers must be of an energy to stimulate a contraction in the area of stimulation of a heart. If the energy of a pulse lies below the threshold level of the heart, no contraction will occur. In the past, clinicians were recommended to set the amplitude of the pulse to double the threshold amplitude value to ensure capture of the stimulation pulse. Recently, however, systems have been developed to allow this amplitude to be reduced to a level closer to the threshold value which results in obvious power savings. In such a system, the stimulation pulse energy can be reviewed, for instance periodically or on determination of a failed stimulation, to determine the optimal power level for reliable stimulation. This may be accomplished by progressively reducing the stimulating pulse energy over a number of stimulation cycles until no evoked response is detected. Once this critical energy level has been found, the stimulation pulse energy can be raised to the lowest level which resulted in an evoked response, with a safety margin of a few tenths of a volt added thereto, and this level is maintained until the next threshold check. Outside of this checking procedure, any stimulation pulse that fails to generate an evoked response will cause the pacer to raise the stimulation pulse energy until capture is attained once again. In both the procedures described above, a failure to evoke a response results in a backup pulse being emitted immediately to prevent discomfort to the patient. The backup pulse is a pulse of an energy level designed to guarantee a response in the heart.

In dual chamber cardiac pacers of the type described above, which include pacers operating in the DDI, DVI, DDD and VDD modes, it may be of interest to lengthen the interval between either the sensed atrial event or atrial stimulation pulse and ventricular stimulation to detect the underlying intrinsic rhythm of the heart. These intervals are commonly collectively termed the A-V interval. Correctly, the A-V interval refers only to the interval between atrial stimulation and ventricular stimulation, i.e. generation of an "A" pulse and a "V" pulse, while the interval between a sensed natural atrial event (a P-wave) and ventricular stimulation is called the P-V interval. However for the purposes herein, the collective expression A-V interval will be used to denote both situations unless otherwise specified. If the intrinsic rhythm of ventricular depolarization is acceptable, it may be beneficial to utilize this spontaneous activity rather than pacing the heart artificially in some situations, since this saves power. Thus if spontaneous ventricular activity is detected in the lengthened A-V interval, ventricular stimulation could be inhibited so that the spontaneous activity drives the heart while this is possible.

In the systems described above, however, wherein the pacer is configured to adapt its pacing pulse energy to the threshold of the heart, a ventricular stimulation pulse delayed to detect intrinsic activity may fail to evoke a response in the heart. This may be due to a momentary incorrect pulse energy level, or can occur, for example, when a spontaneous ventricular beat is coincident or almost coincident with the stimulation pulse and cannot be detected by the pacer. Such an event is commonly called a fusion or pseudo fusion beat. In order to ensure capture, the pacer will then transmit a backup pulse in the normal manner. Since the backup pulse is generated only after the pacer has determined that no response is evoked, there is an additional delay before the heart receives a successful pacing signal. This further delay might cause the pacer to detect a retrograde P-wave, possibly causing the heart to go into to pacemaker mediated tachycardia.

There is thus a need for a cardiac pacer operating in dual-chamber mode that is capable of operating in a power-saving manner while providing the heart with reliable and safe stimulation.

SUMMARY OF THE INVENTION

The above need is satisfied in a dual chamber cardiac pacemaker in accordance with the invention, including a unit which identifies a beginning of an A-V interval, a ventricular pulse generator which emits ventricular stimulating pulses, a ventricular sensor for sensing ventricular depolarization, and a control unit connected to the ventricular pulse generator for causing a ventricular pulse of a predetermined energy level to be emitted after expiration of the A-V interval. The control unit also prolongs the A-V interval under certain circumstances, and causes the ventricular pulse generator to emit a ventricular pulse at a higher energy level than said predetermined energy level after the expiration of the prolonged A-V interval.

The A-V interval is defined as a predetermined time period starting with either the sensing of atrial depolarization or the generation of an atrial stimulus pulse. Therefore, the unit for identifying the beginning of the A-V interval can be an atrial pulse generator or an atrial sensor for sensing events in the atrium.

By utilizing a high energy pulse after prolonging the A-V interval it can be assumed that a response has been evoked in the heart. Thus there is no need to monitor the heart after emitting this pulse and no backup pulse is required. In this way the total delay between an atrial event, whether stimulated or spontaneous, and the subsequent ventricular stimulus pulse can be kept at a length permitting any underlying intrinsic rhythm to be detected while ensuring the correct interaction of the pacer with the patient. Furthermore, the lower energy ventricular stimulus pulse energy can be retained for operation with the normal A-V interval, so the overall power required for stimulation is kept low.

Preferably, the delivery of the high energy pulse is inhibited if a spontaneous ventricular event is detected. The heart can thus be permitted to function spontaneously while this is possible. To this end, if a spontaneous ventricular event inhibits the delivery of a high energy pulse, the subsequent A-V interval is preferably similarly prolonged and the same high energy pulse transmitted.

The prolongation of the A-V interval may be actuated when ventricular stimulation after the A-V interval in a previous cycle was unsuccessful. The prolongation of the A-V interval may also or alternatively be set to occur intermittently or periodically, for example, after the elapse of a predetermined time period. For example this may be set to occur once every 8 hours, every 24 hours, every 48 hours or after longer or shorter periods depending on the needs of the patient.

DESCRIPTION OF THE DRAWINGS

FIG. 3 is a further timing diagram illustrating the adaptation of the pacing pulse to the threshold.

FIG. 4 is a timing diagram showing a search for spontaneous heart activity.

DESCRIPTION OF THE PREFERRED EMBODIMENTS

Figure 1:
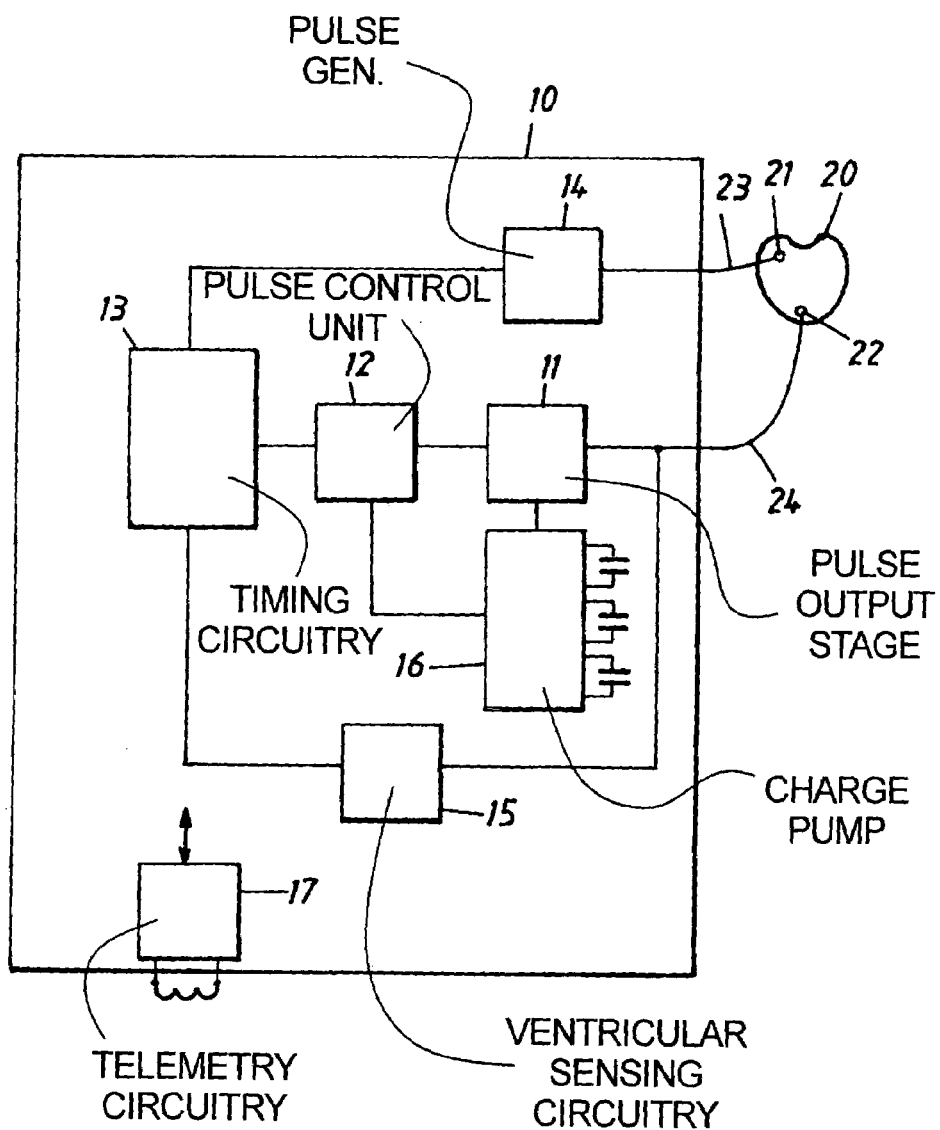
FIG. 1 is a block diagram of a cardiac pacemaker constructed and operating in accordance with the principles of the present invention.

FIG. 1 shows a cardiac pacer connected to a human heart 20. Two pacing electrodes 21, 22 are embedded in the tissue of the heart 20. An atrial electrode 21 is inserted in a location to efficiently evoke a response in the atrial chambers of the heart. The other ventricular electrode 22 is inserted at a location best suited to evoke a response from the ventricular chambers of the heart. The ventricular electrode 22 is connected through a lead 24 to a voltage pulse output stage 11, which in turn is connected to a pulse control unit 12. The atrial electrode 21 is connected to a pulse generator 14 through a second lead 23. Both the pulse generator 14 and the pulse control unit 12 are connected to timing circuitry 13. It will be understood that the atrial electrode 21 may serve as a sensor and relay information on intrinsic or evoked atrial events to associated sensing circuitry (not shown) in the pacer.

The pulse output stage 11 is moreover coupled to a charge pump 16 for providing different voltage amplitudes for ventricular stimulus pulses. The pulse control unit 12 controls both the charge pump 16 and the pulse output stage 11. The pulse control unit 12 thus determines both the amplitude and duration of a ventricular stimulus pulse.

The ventricular electrode 22 is further connected to sensing circuitry 15 via the 25 lead 24. The sensing circuitry 15 detects ventricular activity and may incorporate some timing and logic circuitry to inhibit detection during certain periods. The sensing circuitry 15 is similarly connected to the timing circuitry 13.

The timing circuitry 13 determines the timing of all pulses and communicates this information to the pulse control unit 12 and the pulse generator 14.

The ventricular electrode 21 is preferably bipolar and configured for bipolar sensing and unipolar stimulation. The atrial electrode may be either bipolar or unipolar.

Telemetry circuitry 17 having an inductive coil is further provided for enabling the external programming of various values in the pacer arrangement.

The pulse output stage 11, pulse control unit 12, timing circuitry 13, charge pump 16, sensing circuitry 15, pulse generator 14 and telemetry circuitry 17 are all encapsulated in an implantable conductive housing 10. In the present embodiment the housing 10 serves as an indifferent electrode, however, it will be understood that a separate indifferent electrode may be provided instead.

Figure 2:
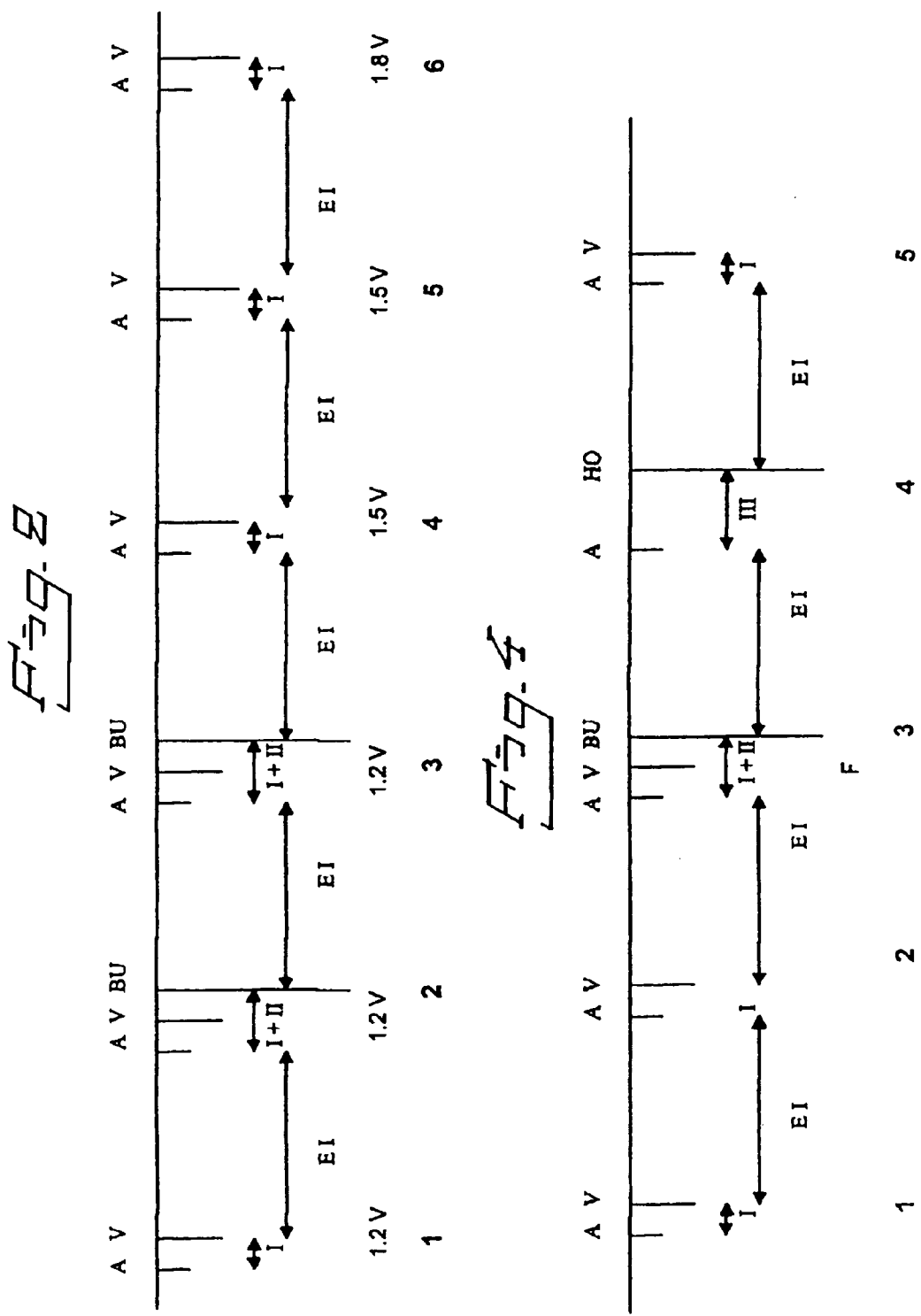
FIG. 2 is a timing diagram illustrating the adaptation of a pacing pulse to the threshold of a heart.

FIGS. 2 and 3 depict a series of timing diagrams showing the adaptation of the pacing pulse energy to the threshold energy level of the heart. In these and the subsequent FIG. 4, A represents an atrial pulse, V a ventricular pulse and BU a backup pulse. It will be appreciated that A may also represent the sensed atrial depolarization, for instance when no atrial stimulation is provided. I is the A-V (P-V) interval, H is the interval between emitting a ventricular pulse and transmitting a backup pulse. El is the escape interval.

FIG. 2 shows a sequence of stimulus pulses when the energy threshold of the heart, that is the minimum energy required to stimulate ventricular depolarization, increases suddenly. At the first cardiac cycle, designated by I in the diagram, an atrial pulse is delivered, followed after expiration of the A-V interval by a ventricular pulse of 1.2 Volts. This results in capture, i.e. a response is evoked and detected by the sensing circuitry 15; the cycle is thus terminated. At point 2, the ventricular pulse of 1.2 Volts does not evoke a response. The timing circuitry 13 then causes the pulse control unit 12 to generate a higher voltage backup pulse at the expiration of the interval ll. This pulse is at a voltage level that guarantees stimulation of the ventricle and is set in the present embodiment at about 4.5 Volts. The escape interval El separating the second cardiac cycle from the third is calculated from the backup pulse BU rather than from the ventricular pulse V. In the next cycle depicted at 3, the same situation occurs. No capture is obtained with a ventricular pulse of 1.2 Volts so a backup pulse is generated. Two consecutive losses causes the pulse control unit 12 to increase the energy of the ventricular stimulus pulse. This is preferably done by increasing the voltage amplitude. In the next cycle shown at 4, a ventricular pulse of 1.5 Volts is generated, which results in capture. This result is confirmed in cycle 5. The ventricular pulse voltage is then assumed to approximate the threshold level of the heart. In order to ensure reliable functioning of the pacer, a safety margin of 0.3 Volts is added to the pulse amplitude resulting in a pulse voltage amplitude of 1.8 Volts. This is utilized in cycle 6. This amplitude is the new pulsing level for ventricular stimulation until a further rise in the threshold level results in two consecutive losses, or alternatively a periodic test of the threshold is performed.

FIG. 3 depicts a threshold test which is performed at regular intervals, preferably about once every 8 hours. The time for performing a test is determined by a counter, which is reset when a test is performed, or when the pulse voltage is adjusted in response to a loss. The interval between tests can be programmed externally through the telemetry circuitry 17.

At cycle 1 in FIG. 3 an atrial pulse A is followed after expiration of the A-V (P-V) interval l by a ventricular pulse of 1.5 Volts. In cycle 2, this voltage level is reduced to 1.2 Volts, which results in capture. This result is confirmed in cycle 3. In cycle 4, the ventricular pulse voltage is reduced still further to 0.9 Volts. This also results in capture. This result is then successfully confirmed in cycle 5. In cycle 6, the voltage is reduced to 0.6 Volts, which results in loss. A backup pulse of 4.5 Volts is delivered after a delay ll. This loss is confirmed in cycle 7, whereupon the voltage is raised again to 0.9 Volts in cycle 8. This again results in capture. This is repeated in cycle 9 which confirms that the new threshold level is 0.9 Volts. The safety margin of 0.3 Volts is added, and the final pulse voltage level of 1.2 Volts attained in cycle 10. This voltage level is retained until the next threshold review.

Due to the occurrence of random intrinsic events, a spontaneous beat may occur simultaneously with a ventricular stimulation pulse, resulting in a so-called fusion or pseudo fusion beat. Such a beat is interpreted as a loss by the sensing circuitry 15 and results in the transmission of a backup pulse, although a backup pulse is superfluous at this point It can thus be interesting to prolong the A-V interval in order to determine whether an intrinsic heart rhythm is present. This is shown in FIG. 4. Cycles 1 and 2 of FIG. 4 occur normally, that is, an atrial pulse is followed by a ventricular pulse after the standard A-V interval 1 and capture occurs in both cases. The A-V interval typically lies at around 170 ins. In the cycle 3, no capture occurs due to a fusion or pseudo fusion beat which is indicated by F. This is interpreted as a loss, and a backup pulse EU is transmitted. In the subsequent cycle 4, a prolonged delay HI is used in place of the A-V interval 1. The prolonged interval m is preferably between 40 ins and 150 ins longer than the standard A-V interval, resulting in a total interval of between about 210 ins and 320 ms. At the expiration of this delay, a high output pulse HO is generated and delivered to the ventricle of the heart 20. The energy of the high output pulse HO is chosen to ensure that capture will occur, providing that it is not coincident with spontaneous activity or with the refractory period of the ventricle. The high energy pulse is thus selected to have an energy equivalent to at least double that of the threshold of the heart. The energy of the high output pulse HO may be set at twice the threshold determined previously as described with reference to FIGS. 2 and 3. However, the voltage level of the high energy pulse HO is preferably fixed at a predetermined level. A preferred voltage level for the high energy pulse is at least 3 volts and more preferably at least 4 volts. Usefully, the high energy pulse HO can have an energy equivalent to that of the backup pulse BU, that is 4.5 V. Since the high energy pulse HO guarantees capture, there is no need to transmit a backup pulse BU in the event of loss, and the A-V interval will not be further prolonged. In the illustrated embodiment the high output pulse HO has a voltage level of 4.5 Volts. This results in capture, and in the subsequent cycle a ventricular pulse V is generated at the previously utilized energy. It is to be noted that when generating a high output pulse HO, the escape interval El is calculated from this pulse HO.

If spontaneous activity is detected by the sensing means 15 during the prolonged delay III, the high output pulse HO is inhibited. In the following cycle, the prolonged delay III is used again in place of the A-V interval 1 to allow spontaneous activity to drive the heart in place of the pacer. This continues until no spontaneous activity is detected during the period III. Preferably the escape interval El following a sequence of inhibited high output pulses HO is reduced to diminish the risk of fusion beats.

If the high output pulse does not result in capture, it is assumed that a fusion 25 beat has occurred and the normal A-V interval is utilized in the following cycle. No backup pulse BU is transmitted. The prolonged cardiac cycle has no influence on the review of the threshold level.

The prolonging of the A-V interval may be programmed to occur at regular intervals, for example at least once every 8 or 12 hours. Alternatively, or in addition, it may be triggered by a loss, which may be due to a fusion beat.

The duration and frequency of use of the prolonged A-V interval can be programmed externally through the telemetry circuitry 17.

While in the described embodiment the high energy pulse HO transmitted after the prolonged A-V interval is obtained by increasing the voltage amplitude, it will be understood that the energy of this stimulus may also be obtained by increasing the pulse duration compared to a normal ventricular pulse V.

Although modifications and changes may be suggested by those skilled in the art, it is the invention of the inventor to embody within the patent warranted heron all changes and modifications as reasonably and properly come within the scope of his contribution to the art.

I claim:

1. A dual chamber cardiac pacemaker comprising:
   a unit that identifies a beginning of an A-V interval of a heart;
   a ventricular sensor adapted to interact with the heart to sense ventricular depolarization of the heart;
   a ventricular pulse generator adapted to interact with the heart to emit ventricular stimulation pulses to the ventricle of the heart; and
   a programmable control arrangement connected to said ventricular pulse generator and to said unit that identifies a beginning of said A-V interval, programmed to cause said ventricular pulse generator to generate a ventricular stimulation pulse at a predetermined energy level after expiration of said A-V interval, and to prolong said A-V interval dependent on occurrence of a predetermined event, and to cause said ventricular pulse generator to emit a ventricular stimulation pulse at a higher energy level than said predetermined energy level after expiration of said prolonged A-V interval.

2. A pacemaker as claimed in claim 1 wherein said control arrangement is programmed to cause said ventricular pulse generator to generate said ventricular stimulation pulse at said higher energy level at an energy level which is at least double a threshold level of said heart.

3. A pacemaker as claimed in claim 1 wherein said control arrangement is programmed to cause said ventricular pulse generator to generate said ventricular pulse at said higher energy level at a voltage of at least 3 V.

4. A pacemaker as claimed in claim 1 wherein said control arrangement is programmed to cause said ventricular pulse generator to generate said ventricular pulse at said higher energy level at a voltage of at least 4 V.

5. A pacemaker as claimed in claim 1 wherein said ventricular sensor is connected to said control arrangement, and wherein said arrangement is programmed to inhibit said ventricular pulse generator from emitting said ventricular stimulation pulse at said higher energy level if ventricular depolarization is sensed by said ventricular sensor during said prolonged A-V interval.

6. A pacemaker as claimed in claim 5 wherein said control arrangement is programmed to prolong said A-V interval in a subsequent cardiac cycle following inhibition of emission of said higher energy pulse by said ventricular pulse generator.

7. A pacemaker as claimed in claim 1 wherein said control arrangement is programmed to cause said ventricular pulse generator to emit said higher energy pulse with a higher voltage amplitude than said ventricular stimulation pulse at said predetermined energy level.

8. A pacemaker as claimed in claim 1 wherein said control arrangement is programmed to cause said ventricular pulse generator to emit said higher energy pulse with a longer duration than said ventricular stimulation pulse at said predetermined energy level.

9. A pacemaker as claimed in claim 1 wherein said ventricular sensor is connected to said control arrangement, and wherein said control arrangement is programmed to cause said ventricular pulse generator to emit a back-up ventricular pulse if said ventricular sensor detects no ventricular depolarization following emission of said ventricular stimulation pulse of said predetermined energy level.

10. A pacemaker as claimed in claim 9 wherein said control arrangement is programmed to cause said ventricular pulse generator to emit said back-up pulse with a same energy level as said higher energy level pulse.

11. A pacemaker as claimed in claim 1 wherein said ventricular pulse generator sets said predetermined energy level of said ventricular stimulation pulse dependent on a threshold level of said heart.

12. A pacemaker as claimed in claim 1 wherein said control arrangement is programmed to cause said prolonged A-V interval to exceed said A-V interval in a range between 40 ms and 150 ms.

13. A pacemaker as claimed in claim 1 wherein said control arrangement is connected to said ventricular sensor, and said control arrangement is programmed to prolong said A-V interval if said ventricular sensor fails to detect depolarization in said ventricle after generation of a ventricular stimulation pulse of said predetermined energy level and before termination of said A-V interval.

14. A pacemaker as claimed in claim 1 wherein said control arrangement is programmed to prolong said A-V interval after expiration of a predetermined time period.

15. A pacemaker as claimed in claim 1 wherein said unit that identifies a beginning of said A-V interval is an atrial pulse generator adapted to interact with the heart to emit atrial stimulation pulses to an atrium of the heart.

16. A pacemaker as claimed in claim 1 wherein said unit that identifies a beginning of said A-V interval is an atrial sensor adapted to interact with the heart to sense atrial depolarization of the heart.

* * * * *